US010646402B2

(12) United States Patent
Momose et al.

(10) Patent No.: US 10,646,402 B2
(45) Date of Patent: May 12, 2020

(54) SYRINGE DEVICE FOR COMMUNICATING TWO TYPES OF SUBSTANCES TO EACH OTHER AND METHOD THEREOF

(71) Applicant: KAKEN PHARMACEUTICAL CO., LTD., Tokyo (JP)

(72) Inventors: Noboru Momose, Shizuoka (JP); Takuya Sugimoto, Tokyo (JP); Norio Watanabe, Shizuoka (JP)

(73) Assignee: KAKEN PHARMACEUTICAL CO., LTD., Tokyo (JP)

(*) Notice: Subject to any disclaimer, the term of this patent is extended or adjusted under 35 U.S.C. 154(b) by 53 days.

(21) Appl. No.: 15/764,085

(22) PCT Filed: Sep. 30, 2016

(86) PCT No.: PCT/JP2016/078973
§ 371 (c)(1),
(2) Date: Mar. 28, 2018

(87) PCT Pub. No.: WO2017/057659
PCT Pub. Date: Apr. 6, 2017

(65) Prior Publication Data
US 2019/0053982 A1 Feb. 21, 2019

(30) Foreign Application Priority Data
Sep. 30, 2015 (JP) .................................. 2015-193768

(51) Int. Cl.
*A61J 1/20* (2006.01)
*A61M 5/178* (2006.01)
*A61J 3/00* (2006.01)

(52) U.S. Cl.
CPC ............... *A61J 1/2013* (2015.05); *A61J 1/20* (2013.01); *A61J 1/2096* (2013.01); *A61J 3/00* (2013.01); *A61M 5/178* (2013.01); *A61M 5/1782* (2013.01)

(58) Field of Classification Search
CPC ...... A61J 1/2013; A61J 1/2048; A61J 1/2089; A61J 1/2096; A61M 5/178; A61M 5/1782; A61M 5/19
See application file for complete search history.

(56) References Cited

U.S. PATENT DOCUMENTS 7,077,835 B2 * 7/2006 Robinson .............. A61J 1/2089
604/413
7,597,680 B2 * 10/2009 Watanabe ............. A61J 1/2096
604/533
(Continued)

FOREIGN PATENT DOCUMENTS

CN 102844064 A 12/2012
EP 1 849 448 A1 10/2007
(Continued)

OTHER PUBLICATIONS

International Search Report for PCT/JP2016/078973 dated Oct. 25, 2016 [PCT/ISA/210].
(Continued)

*Primary Examiner* — Matthew W Jellett
(74) *Attorney, Agent, or Firm* — Sughrue Mion, PLLC

(57) ABSTRACT

A syringe device includes an administration holder, and a cylinder portion which allows insertion of the administration holder. The cylinder portion includes a coupling holder, a slit holder coupled to the coupling holder, and a double-ended needle assembly disposed slidably in an interior of the coupling holder. A cartridge for a freeze-dry product is mounted, in the administration holder, and a cartridge for solvent is mounted in the coupling holder. When the admin-
(Continued)

istration holder is pushed, the double-ended needle assembly slides. When one of the needle points pricks the cartridge for freeze-dry product, the other needle point of the double-ended needle assembly pricks the cartridge for the solvent, and then the needle points unseal the cartridges by a further sliding movement of the double-ended needle assembly.

18 Claims, 15 Drawing Sheets

(56) References Cited

U.S. PATENT DOCUMENTS

| | | | | |
|---|---|---|---|---|
| 8,007,461 | B2* | 8/2011 | Huo | A61M 5/31511 |
| | | | | 604/415 |
| 8,088,118 | B2* | 1/2012 | Reynolds | A61J 1/2089 |
| | | | | 604/411 |
| 8,551,068 | B2 | 10/2013 | Kyle et al. | |
| 8,636,689 | B2* | 1/2014 | Halili, Jr. | A61J 1/2096 |
| | | | | 604/88 |
| 9,480,623 | B2* | 11/2016 | Eilertsen | A61J 1/2096 |
| 9,744,102 | B2* | 8/2017 | Kubo | A61J 1/2096 |
| 2008/0177226 | A1 | 7/2008 | Watanabe et al. | |
| 2008/0188828 | A1 | 8/2008 | Reynolds et al. | |
| 2008/0269680 | A1 | 10/2008 | Ibranyan et al. | |
| 2012/0172830 | A1* | 7/2012 | Yokoyama | A61J 1/2089 |
| | | | | 604/413 |
| 2013/0072882 | A1 | 3/2013 | Ogawa et al. | |

FOREIGN PATENT DOCUMENTS

| | | |
|---|---|---|
| JP | 49-77487 A | 7/1974 |
| JP | 5-146510 A | 6/1993 |
| JP | 11-89934 A | 4/1999 |
| JP | 2007-260162 A | 10/2007 |
| JP | 4785831 A1 | 10/2011 |
| JP | 2013-75154 A | 4/2013 |
| JP | 2015-77217 A | 4/2015 |
| WO | 03/016170 A1 | 2/2003 |
| WO | 2006/085546 A1 | 8/2006 |

OTHER PUBLICATIONS

Communication dated Mar. 8, 2019 by the European Patent Office in application No. 16851828.0.

* cited by examiner

A-A CROSS-SECTIONAL VIEW

SYRINGE DEVICE FOR COMMUNICATING TWO TYPES OF SUBSTANCES TO EACH OTHER AND METHOD THEREOF

CROSS REFERENCE TO RELATED APPLICATIONS

This application is a National Stage of International Application No. PCT/JP2016/078973 filed Sep. 30, 2016, claiming priority based on Japanese Patent Application No. 2015-193768 filed Sep. 30, 2015.

TECHNICAL FIELD

The present invention relates to a syringe device used for communicating two types of substances to each other and a method of communicating the two types of substances to each other by using the syringe device.

BACKGROUND ART

Conventionally, such a technology as described in Patent Document 1 has been existing as a syringe device and a method of preparing drugs using the device.

Patent Document 1 discloses a syringe device including: a cylindrical coupling holder (6); an intermediate holder (3); a first syringe (1) with a bottomed cylindrical shape configured to store a solvent and having an unsealably sealed distal bottom portion; a second syringe (2) with a bottomed cylindrical shape configured to store a dissolvable drug and having an unsealably sealed distal bottom portion; and a double-ended needle assembly (10).

In the syringe device disclosed in Patent Document 1, as a first step, the distal bottom portion of the first syringe (1) is unsealed with one needle point (55b) of a double-ended needle assembly (10) by inserting and pushing a push rod (15) into the first syringe (1). At this time, the intermediate holder (3) is locked by locking means at a stand-by position, where the double-ended needle assembly (10) at an initial position is not affected. Subsequently, as a second step, the intermediate holder (3) is unlocked and the intermediate holder (3), being in the first cylindrical portion (11), is then pushed toward a partition wall (31) so that the double-ended needle assembly (10) is pushed to move to a second position, and the distal bottom portion of the second syringe (2) is unsealed by other needle point (55a) of the double-ended needle assembly (10). The push rods (15, 16) inserted into the respective syringes (1, 2) are pushed alternately in a state in which the both syringes (1, 2) are in communication with each other via the double-ended needle assembly (10), whereby the solvent gets mixed with and dissolves the drug to produce a liquid medication.

In this manner, in Patent Document 1, the distal bottom portions of the first and second syringes is unsealed by both needle points of the double-ended needle assembly (10) by a two-step pushing operation, and during the two-step operation, another operation is required for unlocking the intermediate holder.

In general, in a device configured to prepare a mixed solution by using a drug filled container and a solvent filled container, the drug filled container is held in a decompressed state in terms of stability of a drug and a sealing performance of the container in many cases, and a double-ended needle is generally used for communicating the mixed solution to each other between the two containers.

However, the technical field of the device as described above has a common drawback as follows. In other words, when one of needle points of the double-ended needle penetrates through a rubber packing or a rubber plug of the drug filled container before the solvent filled container is penetrated, entry of air from the other needle point of the double-ended needle into the decompressed rubber packing is likely to occur. In this manner, when air flows into the drug filled container, this may cause oxidation, decomposition, and transformation of effective components, as well as remarkable increase in volume of the prepared liquid medication, which may hinder adequate administration. In contrast, when the one of the needle points of the double-ended needle penetrates through the solvent filled container first, liquid leakage may occur through the other needle point of the double-ended needle from the container.

CITATION LIST

Patent Document

Patent Document 1: Japanese Patent No. 4785831

SUMMARY OF INVENTION

Technical Problem

In view of the above circumstances, it is an object of the present invention to provide a syringe device and a method capable of creating a state in which two types of substances are communicated to each other via the double-ended needle assembly by a one-step continuous push operation and reducing a probability of entry of air or liquid leakage at that time.

Solution to Problem

In order to solve the above-described problem, a syringe device of the present invention includes: an administration holder including a first storage chamber; a hollow cylinder portion; and a double-ended needle assembly including a first needle point and a second needle point, the cylinder portion including: a holder sliding portion configured to slidably retain the administration holder inserted at least partly from one end of the cylinder portion until a front end portion of the first storage chamber reaches a predetermined position; a second storage chamber provided on the other end side of the cylinder portion; a double-ended needle sliding portion formed between the holder sliding portion and the second storage chamber, wherein in the double-ended needle sliding portion the double-ended needle assembly can slide from a first position closer to the administration holder to a second position closer to the second storage chamber; wherein the first needle point is at a position closer to the one end than the predetermined position and the second needle point does not reach the second storage chamber when the double-ended needle assembly is at the first position, the second needle point reaches an interior of the second storage chamber and the first needle point is at a position closer to the one end than the predetermined position when the double-ended needle assembly is at the second position, and the first needle point reaches an interior of the first storage chamber when a front end portion of the first storage chamber is at the predetermined position.

According to a preferred embodiment of the present invention, a first cartridge configured to store a first substance is mounted in the first storage chamber, a second cartridge configured to store a second substance is mounted in the second storage chamber, and the first and second cartridge respectively include at front end portions thereof sealing members configured to be pricked by the first and second needle points of the double-ended needle assembly. When the administration holder is slid toward the second cartridge in the holder sliding portion, the first needle point pricks the sealing member of the first cartridge without unsealing the same, and in this state, the administration holder slides in the holder sliding portion, and the double-ended needle assembly slides toward the second position accordingly. While the double-ended needle assembly slides toward the second position, the second needle point pricks the sealing member of the second cartridge in a state in which the first needle point pricks the sealing member of the first cartridge without unsealing the same, and thus the double-ended needle assembly is temporarily in a closed state. The first needle point unseals the sealing member of the first cartridge, the second needle point unseals the second cartridge, and the first and second cartridges communicate with each other through the double-ended needle assembly before the sealing member of the first cartridge reaches the predetermined position after the closed state.

The preferable administration holder includes a projecting portion on an outer peripheral portion, and the holder sliding portion includes a punched hole configured to receive the projecting portion and retain the administration holder at an initial position, and a slit extending in the longitudinal direction and configured to guide the projecting portion when moving the administration holder from the initial position. More preferably, a diameter of the punched hole is smaller than a width of the projecting portion, the projecting portion includes an inclined portion toward a distal portion thereof, and an initial speed of pushing the administration holder is controlled by the inclined portion engaging the punched hole. Also preferably, a width of the slit relative to the width of the projecting portion is set to control the speed of the administration holder while being pushed.

The double-ended needle sliding portion of the preferred aspect includes: a hollow body configured to define an internal space in which the double-ended needle assembly slides; a wall formed at a boundary between the hollow body and the second storage chamber and including therein a hole which allows the second needle point to pass through; and a guide groove formed on an inner peripheral wall of the hollow body and extending in a longitudinal direction, the guide groove being configured to guide the projecting portion formed on the double-ended needle assembly therealong.

For example, the first substance is a solid state drug, the second substance is a solvent capable of dissolving the drug, or the second substance is a solid state drug, and the first substance is a solvent capable of dissolving the drug, or both of the first substance and the second substance are mixable liquid-state drugs.

As one aspect, each of the first and second cartridges includes: a cartridge container having a distal end opening, a bottom opening, and a hollow portion; a rubber packing as the sealing member configured to seal the distal end opening of the cartridge container; a cap configured to fix the rubber packing; and a piston configured to be slidably inserted from the bottom opening to the hollow portion, the piston allowing a substance to be stored between the rubber packing and the piston.

Preferably, a plunger rod configured to be mounted on the piston is provided.

Preferably, the administration holder includes a needle insertion portion formed at a position adjacent to the first storage chamber.

Another aspect of the present invention provides a method of communicating a first substance and a second substance to each other using a syringe device, wherein the syringe device includes: an administration holder including a first cartridge configured to store the first substance; a hollow cylinder portion; and a double-ended needle assembly including a first needle point and a second needle point, and a second cartridge configured to store the second substance, the first cartridge and the second cartridge including sealing members respectively, the method including: sliding the administration holder inserted into the cylinder portion along a longitudinal direction of the cylinder portion; allowing the first needle point to prick the sealing member without unsealing the sealing member of the first cartridge; sliding the double-ended needle assembly by sliding the administration holder in a state in which the first needle point pricks a sealing member of the first cartridge, allowing the second needle point to prick the sealing member without unsealing the sealing member of the second cartridge before the first needle point unseals the sealing member of the first cartridge, thereby forming a closed state of the double-ended needle assembly; and unsealing the sealing members of the first and second cartridges by the first needle point and the second needle point by further sliding the administration holder, thereby allowing the first and second cartridges to communicate with each other through the double-ended needle assembly.

Preferably, the sliding the administration holder includes sliding the administration holder along a longitudinal direction of the cylinder portion in one-step operation.

Preferably, the method includes, after allowing the first and second cartridges to communicate with each other through the double-ended needle assembly, mixing the first and second substances by pushing a substance in one of the first and second cartridges outward into the other cartridge, and then pushing the first and second substances mixed in the other cartridge into the one of the cartridge to mix the first and second substances. Preferably, the mixing the first and second substances is repeatedly performed by a plurality of times. For example, the substance in the one of cartridges to be pushed out first is a liquid, and the substance in the other cartridge is a solid or a liquid.

In more preferable aspect, the method further includes: holding the administration holder at an initial position in the cylinder portion before sliding the administration holder, and controlling an initial speed of the administration holder by adjusting a resistance force generated when starting the administration holder to slide from the initial position.

Preferably, the sliding the administration holder further includes: adjusting a frictional force generated between the administration holder and the cylinder portion so as to control a sliding speed while pushing the administration holder.

In the allowing the first and second cartridges to communicate with each other through the double-ended needle assembly, there is executed any one of the followings: a first aspect in which the first needle point unseals the sealing member of the first cartridge and then the second needle point unseals the sealing member of the second cartridge; a second aspect in which the second needle point unseals the sealing member of the second cartridge and then the first needle point unseals the sealing member of the first cartridge; and a third aspect in which the first needle point unseals the sealing member of the first cartridge and simultaneously, the second needle point unseals the second cartridge.

BRIEF DESCRIPTION OF DRAWINGS

FIG. 1(B) is a cross-sectional view taken along a line A-A (FIG. 1(A)) of the syringe device.

FIGS. 3(A) and 3(B) are drawings illustrating a cylinder portion of the syringe device according to the embodiment of the present invention, in which FIG. 3(A) is a front view of the cylinder portion, and FIG. 3(B) is a plan view of the cylinder portion.

FIG. 4(B) is a vertical cross-sectional view of the administration holder taken along a line A-A in FIG. 4(A).

FIG. 5(B) is a vertical cross-sectional view of the coupling holder taken along a line B-B in the right side view in FIG. 5(A), and FIG. 5(C) is a vertical cross-sectional view of the coupling holder taken along a line A-A in the plan view in FIG. 5(A).

FIGS. 6(A) and 6(B) are drawings of a slit holder, which is one of the components of the cylinder portion in FIG. 3, in which FIG. 6(A) is a plan view and left and right side views of the slit holder, FIG. 6(B) is a vertical cross-sectional view and the left and right side view of the slit holder taken along a plane passing through a guide slit.

FIGS. 13(A), 13(B), and 13(C) are cross-sectional views of the syringe device illustrating a state in which a first cartridge is mounted in the administration holder and a second cartridge is mounted in the cylinder portion, in which FIG. 13(A) illustrates a first step in which a double-ended needle is in contact with none of rubber packings of the first and second cartridges, FIG. 13(B) illustrates a second step in which both needle points of the double-ended needle prick the rubber packings of the first and second cartridges but do not penetrate therethrough, and FIG. 13(C) illustrates a third step in which the double-ended needle penetrates through both of the rubber packings of the first and second cartridges.

DESCRIPTION OF EMBODIMENTS

Figure 1A:
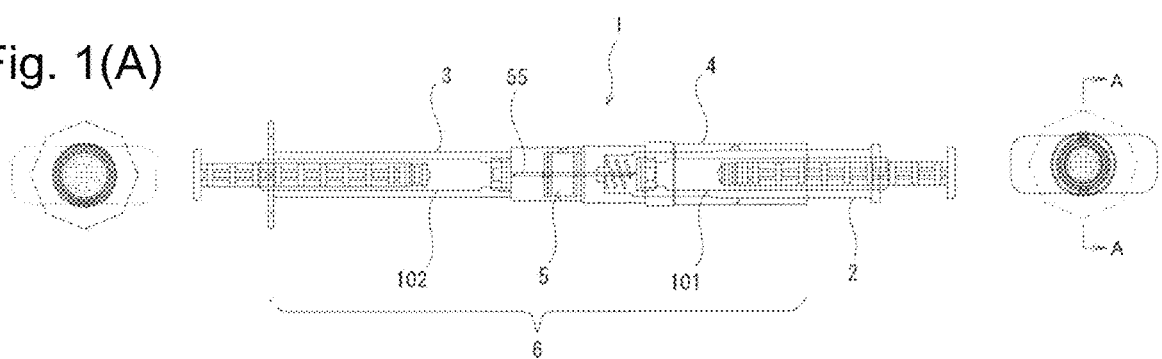
FIGS. 1(A) and 1(B) are drawings of a syringe device according to an embodiment of the present invention, in which FIG. 1(A) includes a front view and left and right side views of the syringe device.
Figure 1B:
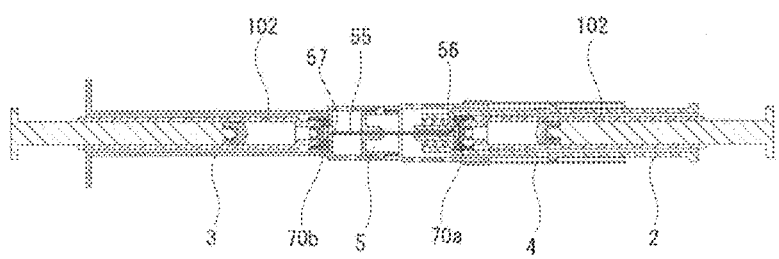
Figure 2:
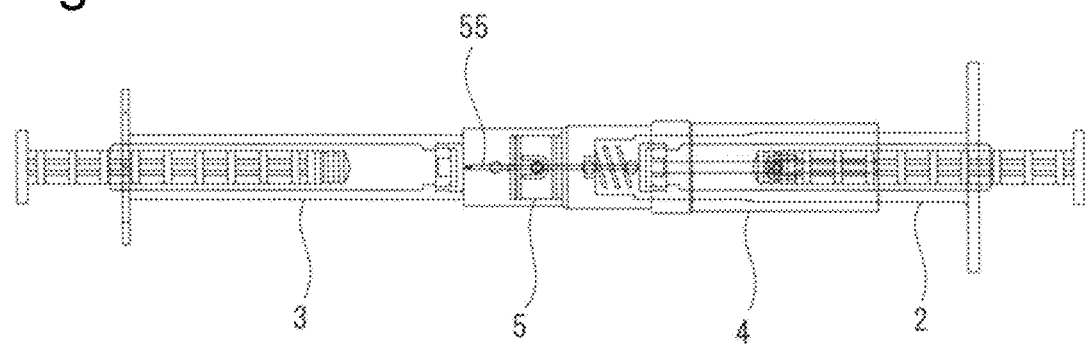
FIG. 2 is a plan view of the syringe device according to an embodiment of the present invention.

Referring now to the drawings, an embodiment of the present invention will be described. FIGS. 1(A), 1(B) and FIG. 2 illustrate a syringe device 1 according to an embodiment of the present invention. The syringe device 1 is used for communicating two types of substances to each other, that is, a first substance and a second substance. The syringe device 1 according to the embodiment is capable of mixing the first and second substances after communicating the first and second substances to each other. As used herein the term "mixing" is intended to include a concept of not only dissolution when a solid is dissolved in a liquid, but also mixture of solids or of liquids having fluidity.

Figure 3A:
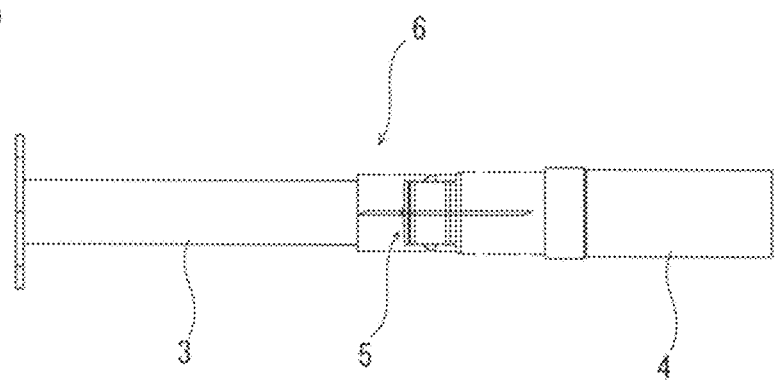
Figure 3B:
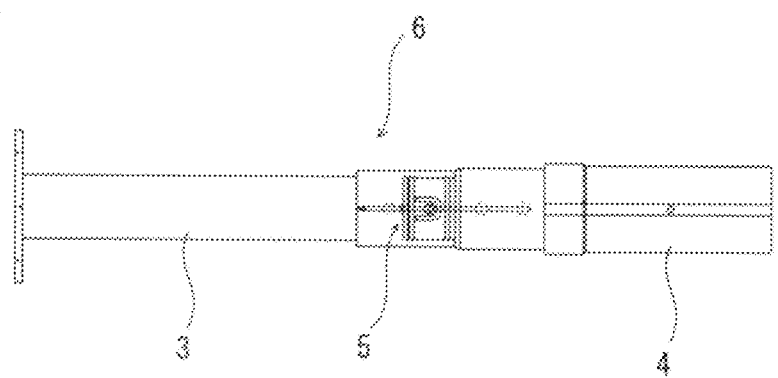

As illustrated in FIGS. 1(A), 1(B), and FIG. 2, the syringe device 1 includes an administration holder 2, and a cylinder portion 6 which allows insertion of the administration holder 2. The cylinder portion 6 includes a coupling holder 3, a slit holder 4 coupled to the coupling holder 3, and a double-ended needle assembly 5 disposed slidably in an interior of the coupling holder 3 as is the most clearly illustrated in FIG. 3. The administration holder 2 is slidably inserted into an interior of the slit holder 4, and a front end portion of the administration holder 2 extends beyond the slit holder 4 into the interior of the coupling holder 3.

In the embodiment, as will be described later, a first cartridge 101 filled with the first substance is loaded in the administration holder 2, and a second cartridge 102 filled with the second substance is loaded in the coupling holder 3 of the cylinder portion 6. For example, when the syringe device 1 is used as a device for dissolving and mixing a freeze-dry product in a solution, the first cartridge 101 is filled with the freeze-dry product and the second cartridge 102 is filled with the solution, or on the contrary, the first cartridge 101 is filled with the solution and the second cartridge 102 is filled with the freeze-dry product. A combination of substances that the syringe device of the present invention intends is not limited to this example, includes any combination in which one of the first and second substances is in a liquid state and the other is in a solid state, and also any combination in which both of the first and second substances are in a liquid state. The solid state substance includes uniform solid state substances as a matter of course, and also powders, mixtures of two or more types of solids, mixtures of solids having different sizes, and the like. The liquid state substance may be of any type as long as it is capable of dissolving or mixing a solid state counterpart. For example, not only a liquid state solvent, but also those having fluidity, such as of a colloid type and a gel type.

Figure 4A:
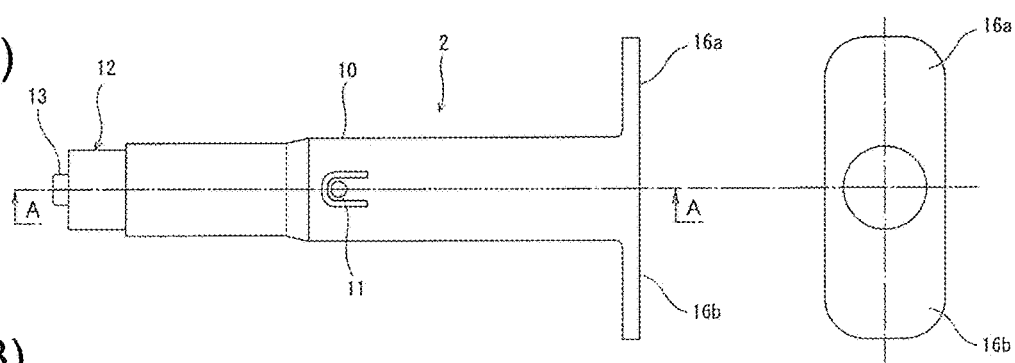
FIGS. 4(A) and 4(B) are drawings of an administration holder, which is one of components of the syringe device in FIG. 1, in which FIG. 4(A) includes a right side view and a plan view of the administration holder.

The administration holder 2 will be described now with reference to FIG. 4(A) and FIG. 4(B).

As illustrated in FIG. 4, the administration holder 2 includes a body segment 10 formed into a hollow shape, a needle insertion portion 12 extending forward from the body segment 10, and a pair of finger hooking projecting strips 16a, 16b formed at a rear end portion of the hollow body segment 10 so as to extend outward at 180 degrees apart from each other in a circumferential direction.

Figure 4B:
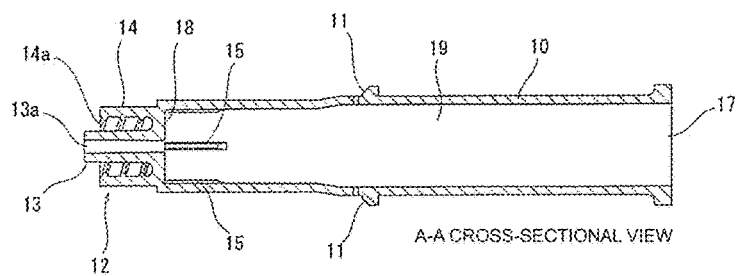

The needle insertion portion 12 includes a central projection 13, a surrounding portion 14 surrounding the periphery thereof in a ring shape, and an inner wall 18 as illustrated in FIG. 4(B). The surrounding portion 14 is provided with a thread 14a on an inner peripheral wall thereof, and a needle insertion hole 13a formed so as to penetrate through the central projection 13. The body segment 10 is partitioned by the inner wall 18 of the needle insertion portion 12 at a front end portion and is provided with an opening 17 formed at a rear end portion. A hollow space in an interior of the body segment 10 defines a first storage chamber 19 for accommodating the first cartridge 101 for one of two drugs to be mixed (the "freeze-dry product" in the embodiment). One end of a needle inserted into the needle insertion hole 13a is allowed to extend from the inner wall 18 into an interior of the first storage chamber 19.

On an inner peripheral wall of the body segment 10 in the vicinity of the needle insertion portion 12, four locking ribs 15 extending by a predetermined length in a longitudinal direction of the administration holder equidistantly in a circumferential direction. The locking ribs 15 function to lock the cartridge when the corresponding cartridge is inserted into the first storage chamber 19. In addition, the body segment 10 is provided on an outer surface thereof with a pair of projecting portions 11 projecting respectively outward at 180 degrees apart from each other in the circumferential direction.

Subsequently, the coupling holder 3 will be described now with reference to FIGS. 5(A), 5(B), and 5(C).

Figure 5A:
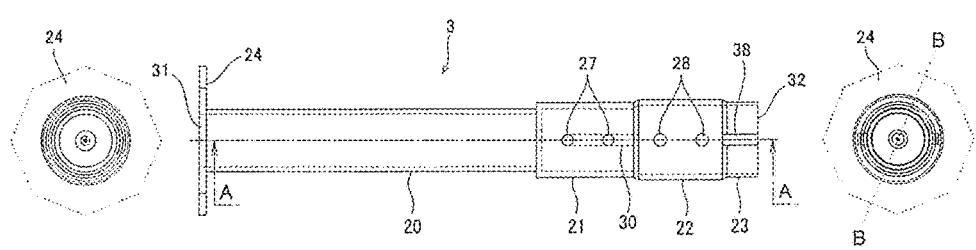
FIGS. 5(A), 5(B), and 5(C) are drawings of a coupling holder, which is one of components of the cylinder portion in FIG. 3, in which FIG. 5(A) includes a plan view, and left and right side views of the coupling holder.
Figure 5B:
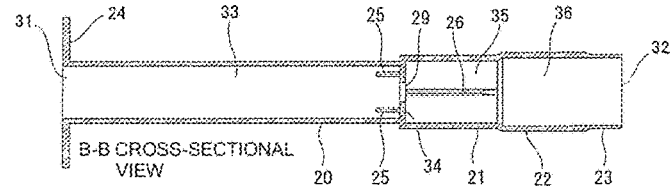
Figure 5C:
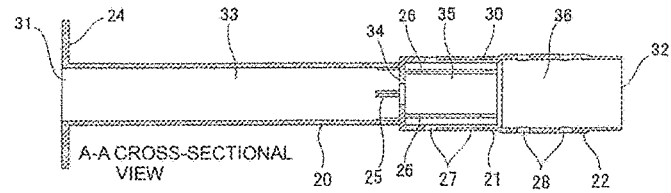

As illustrated in FIG. 5(A), the coupling holder 3 includes a first body segment 20, a second body segment 21 having a larger diameter than the first body segment 20, a third body segment 22 having a larger diameter than the second body segment 21, and a fourth body segment 23 having a smaller diameter than the third body segment 22.

The first body segment 20 is provided at a rear end portion thereof with an opening 31, and in addition, a polygonal projecting strip 24 formed to surround the opening 31. A wall 34 is formed at a boundary between the first body segment 20 and the second body segment 21, and the wall 34 is provided with a needle passage hole 29 formed therethrough. On an inner peripheral wall of the first body segment 20, four locking ribs 25 are formed in the vicinity of the wall 34 so as to extend by a predetermined length in the longitudinal direction of the coupling holder equidistantly in a circumferential direction. A hollow space in an interior of the first body segment 20 defines a second storage chamber 33 for accommodating the second cartridge 102 for one of the two drugs to be mixed (the "solvent" in the embodiment). The locking ribs 25 function to lock the cartridge when the corresponding cartridge is inserted into the second storage chamber 33. One end of a needle passing through the needle passage hole 29 is allowed to extend from the wall 34 into an interior of the second storage chamber 33.

The second body segment 21 defines a double-ended needle sliding space 35 which allows the double-ended needle assembly 5 to slide in a hollow space in an interior thereof. On an inner peripheral wall of the second body segment 21, four ribs 26 are formed to extend in the longitudinal direction of the coupling holder over the entire length of the second body segment 21 equidistantly in the circumferential direction. The double-ended needle assembly 5 is allowed to slide in the longitudinal direction by engagement of an outer surface thereof with a rib 26 and is prevented from moving in a radial direction. The second body segment 21 is also provided with a pair of guide grooves 30 formed respectively on an inner peripheral wall thereof in the longitudinal direction at 180 degrees apart from each other in a circumferential direction, and the guide grooves guide a sliding movement of the double-ended needle assembly 5 as described later. In addition, the second body segment 21 is provided with air holes 27 for improving gas permeability at the time of gaseous sterilization along the guide grooves 30.

The third body segment 22 defines an administration holder in-out space 36 which allows the needle insertion portion 12 of the administration holder 2 to move in and out a hollow space in the interior thereof. The third body segment 22 is also provided with air holes 28 from the same reason as the case of the body segment 21. The third body segment 22 does not have walls at respective boundaries with respect to the second body segment 21 and the fourth body segment 23 to allow the needle insertion portion 12 of the administration holder 2 to pass through the respective body segments 21, 22, 23. The fourth body segment 23 is provided with an opening 32 formed at a rear end portion thereof. The fourth body segment 23 is also provided with a pair of guide slits 38 formed respectively on an inner peripheral wall thereof in the longitudinal direction at 180 degrees apart from each other in a circumferential direction.

Subsequently, the slit holder 4 will be described now with reference to FIGS. 6(A) and 6(B).

Figure 6A:
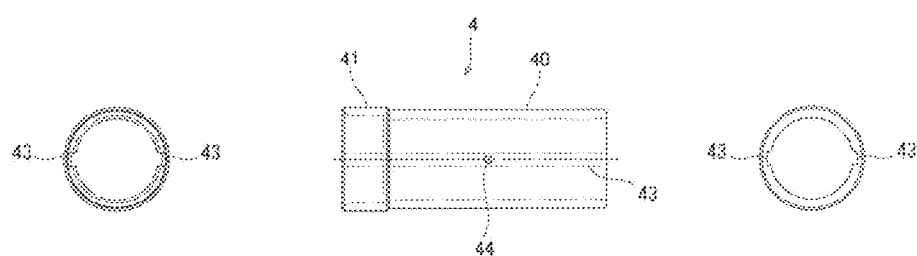
Figure 6B:
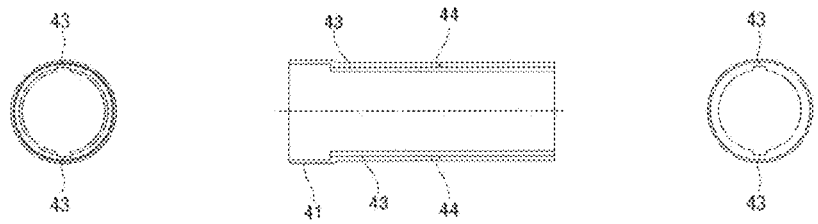

As illustrated in FIG. 6(A), the slit holder 4 includes a main body segment 40 and an engaging body segment 41. The engaging body segment 41 is formed to have a larger outer diameter and an inner diameter than the main body segment 40 and to be engageable with the fourth body segment 23 of the coupling holder 3 by covering the body segment 23. The main body segment 40 is provided with a pair of guide slits 43 formed on an inner peripheral wall thereof respectively in a longitudinal direction at 180 degrees apart from each other in a circumferential direction, and as described later, the guide slits 43 guides a sliding movement of the administration holder 2. The guide slits 43 are coupled to the guide slits 38 of the fourth body 23 of the coupling holder 3. The main body segment 40 is provided with a pair of punched holes 44 to be used for locking the administration holder 2 in the respective guide slits 43 at an initial position. In order to secure a desirable slidability of the administration holder 2, for example, polycarbonate may be selected as a material of the slit holder 4, and for example, polypropylene or ABS resin may be selected as a material of the administration holder 2.

Subsequently, the double-ended needle assembly 5 will be described with reference to FIG. 7.

Figure 7:
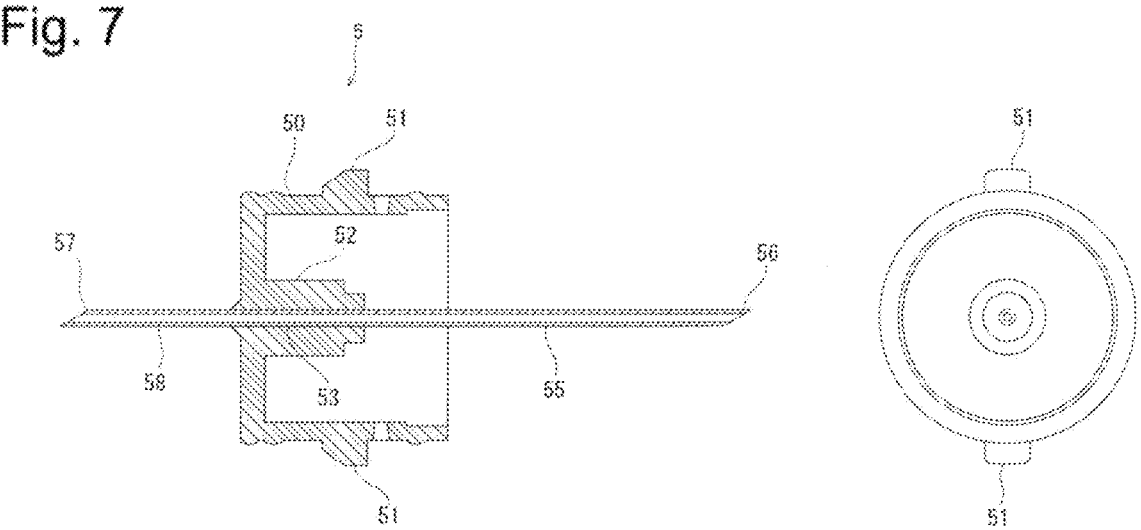
FIG. 7 includes a right side view and a vertical cross-sectional view of a double-ended needle assembly, which is one of the components of the syringe device illustrated in FIG. 1.

As illustrated in FIG. 7, the double-ended needle assembly 5 includes a double-ended needle supporting member 50 and a double-ended needle 55. The double-ended needle supporting member 50 includes a central cylindrical portion 52 formed in an interior of a bottomed cylindrical body, and a pair of projecting portions 51 formed respectively on an outer wall of the bottomed cylindrical body at 180 degrees apart from each other in the circumferential direction, and the central cylindrical portion 52 is provided with a through hole 53 which allows penetration of the double-ended needle 55. The double-ended needle 55 has needle points 56, 57, and a needle through hole 58 is formed between the needle point 56 and the needle point 57. The pair of projecting portions 51 engage one of the pairs of air holes formed on the second body segment 21 of the coupling holder 3 (the pair of air holes 27 on the right side in FIG. 5(C)), respectively before a prick operation. The pair of projecting portions 51 engage the pair of guide grooves 30 formed in the second body segment 21 of the coupling holder 3 respectively and slide along the guide grooves 30 during the prick operation. The pair of projecting portions 51 are fixed in position by engaging the other pairs of air holes formed in the second body segment 21 (the pair of air holes 27 on the left side in FIG. 5(C)) after the prick operation. Accordingly, when the administration holder 2 is pulled out, the double-ended needle assembly 5 is prevented from being pulled out together with the administration holder.

For example, polypropylene or ABS resin may be selected as a material of the double-ended needle assembly 5 and for example polycarbonate may be selected as a material of the coupling holder 3, so that slidability of the double-ended needle assembly 5 may be improved. In addition to the selection of the material of the double-ended needle assembly 5 as described above, a width of the guide grooves 30 relative to the size of the pair of projecting portions 51 is selected as needed so that sliding movement with a predetermined frictional force is achieved along the second body segment 21.

Subsequently, a mechanism for filling the first cartridge 101 and the second cartridge 102 respectively with drugs will be described with reference to FIG. 8 to FIG. 11.

Figure 8:
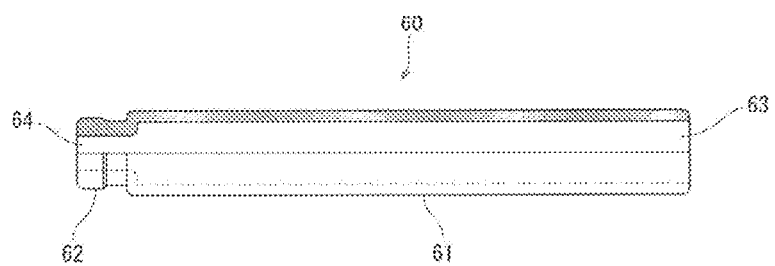
FIG. 8 is a vertical cross-sectional, view of a cartridge to be inserted into interiors of the administration holder and the coupling holder.

FIG. 8 illustrates a cartridge container 60 to be filled with a drug. The cartridge container 60 includes a cartridge body 61 on the bottom side and a head portion 62 on a distal side, and both of portions are formed to have hollow interiors. The cartridge body 61 is provided with a bottom opening 63, and the head portion 62 is provided with a distal end opening 64. In other words, the cartridge container 60 is penetrated through from a distal end to a bottom portion.

Figure 9:
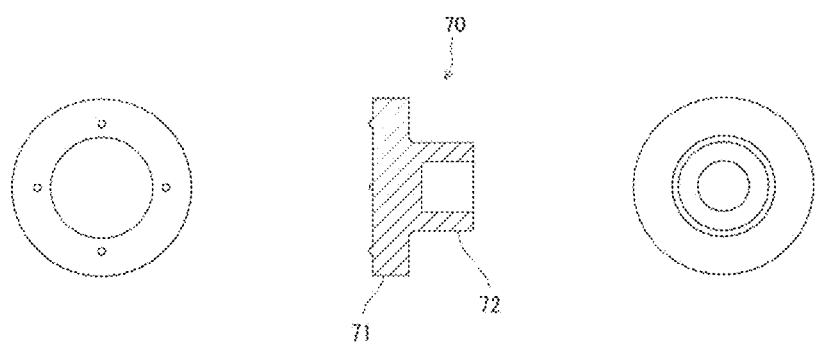
FIG. 9 includes a left side view, a vertical cross-sectional view, and a right side view of a rubber packing for sealing a distal end opening of the cartridge in FIG. 8.

FIG. 9 illustrates a rubber packing 70 to be mounted in the distal end opening 64 of the cartridge container 60. The rubber packing 70 is formed of rubber, and includes a head portion 71 having a large diameter, and a plug portion 72 to be inserted into the distal end opening 64 of the cartridge container 60.

Figure 10:
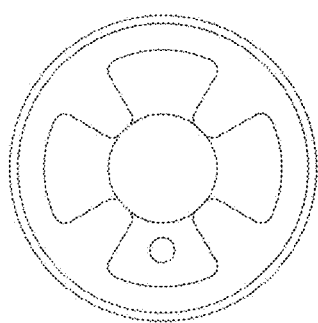
FIG. 10 includes a left side view, a front view (partly in cross section), and right side view of a cap for fixing the rubber packing in a state in which a rubber packing in FIG. 9 seals the distal end opening of the cartridge in FIG. 8.
Figure 10:
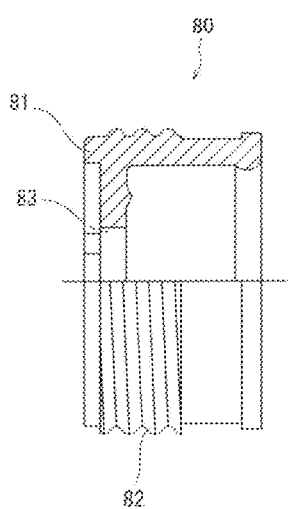
Figure 10:
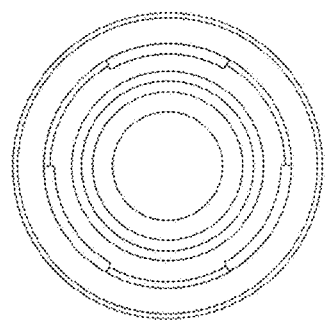

FIG. 10 illustrates a cap 80 for fixing the head portion 62 in a state in which the rubber packing 70 is mounted in the distal end opening 64. The cap 80 includes a bottomed cylindrical body 81, a thread 82 formed on an outer surface of the body 81, and a prick opening 83 formed at a center portion of the bottom portion of the body 81. The thread 82 engages the locking ribs 15 formed on the body segment 10 (FIG. 4(B)) of the administration holder 2 with locking ribs 25 respectively formed on an inner peripheral wall of the body segment 20 of the coupling holder 3 to fix the cartridge container 60 to the first and second storage chambers 19, 33.

Figure 11:
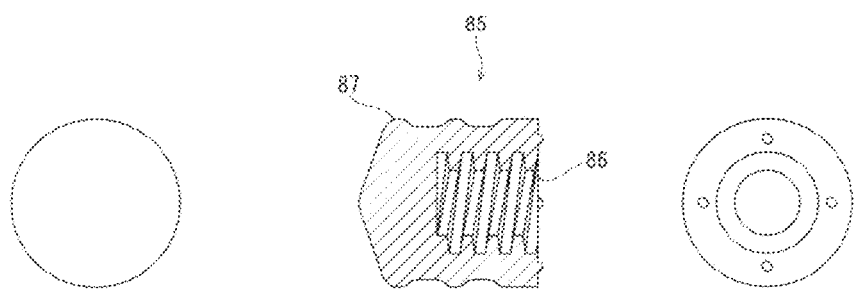
FIG. 11 includes a left side view, a vertical cross-sectional view, and a right side view of a piston configured to seal a first substance and a second substance into an interior of the cartridge together with the rubber packing by being inserted into the interior of the cartridge from a bottom opening of the cartridge in FIG. 8.

FIG. 11 illustrates a piston 85 inserted from the bottom opening 63 of the cartridge container 60 and slidable in an interior of the cartridge container 60. The piston 85 includes a sealing rib 87 configured to engage and seal the inner wall of the cartridge container 60 on an outer surface thereof to prevent a drug from leaking therefrom, and an internal thread 86 formed on an inner peripheral wall of an internal void of the piston 85.

The cartridge container 60 is provided in a state (of cartridge) in which an interior thereof is filled with a drug, a distal side of the cartridge container 60 is sealed by the rubber packing 70 and the cap 80, and the bottom side of the cartridge container 60 is sealed with the piston 85.

Figure 12:
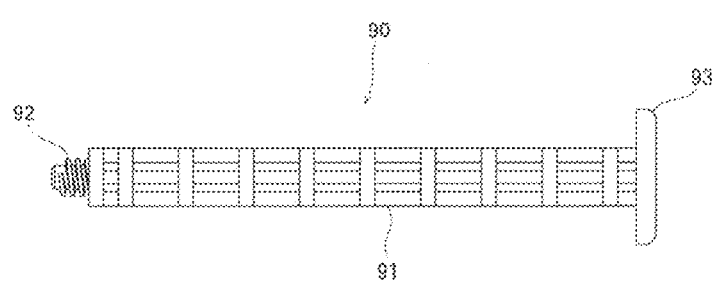
FIG. 12 is a plan view of the plunger rod to be mounted on the piston in FIG. 11.

Note that FIG. 12 illustrates a plunger rod 90 configured to provide the piston 85 with a pressing force by a hand. The plunger rod 90 includes an elongated rod portion 91, a thread portion 92 formed at a distal end of the rod portion 91 so as to be engageable with the internal thread 86 of the piston 85, and a finger placing portion 93 formed on a bottom side of the rod portion 91 and having a large diameter.

Subsequently, an operation of the embodiment of the present invention will be described with reference to FIG. 13 to FIG. 15.

Figure 13A:
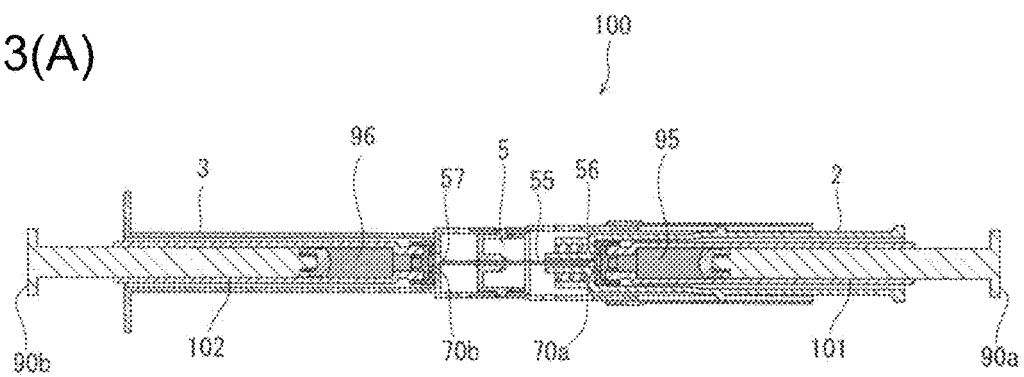

FIG. 13(A) illustrates a syringe device 100 in which the syringe device 1 according to the embodiment of the present invention is filled with two types of drugs. In the syringe device 100 of this embodiment, a first cartridge 101 filled, for example, with a freeze-dry product 95 as a drug is mounted in the first storage chamber 19 of the administration holder 2. The second cartridge 102 filled, for example, with the solvent 96 as a drug is mounted in the second storage chamber 33 of the coupling holder 3. Note that the freeze-dry product 95 is retained in the cartridge container 60 normally in a decompressed state.

In a state of FIG. 13(A), the double-ended needle assembly 5 is disposed at the closest position (a first position) to the administration holder 2 of the double-ended needle sliding space 35. The administration holder 2 is inserted into an initial position in the slit holder 4. At the initial position, the projecting portions 11 of the administration holder 2 are fitted into the punched holes 44 of the slit holder 4 and the administration holder 2 is fixed to the slit holder 4 (see FIG. 15(A)). The needle point 56 of the double-ended needle 55 passes through the needle insertion hole 13a and reaches the position of the inner wall 18, but does not pass the prick opening 83 of the cap 80, and does not prick a rubber packing 70a which seals the freeze-dry product 95. In contrast, the needle point 57 of the double-ended needle 55 stays at the position of the needle passage hole 29 in the interior of the wall 34, does not pass through the prick opening 83 of the cap 80, and does not prick a rubber packing 70b that seals the solvent 96.

Figure 15A:
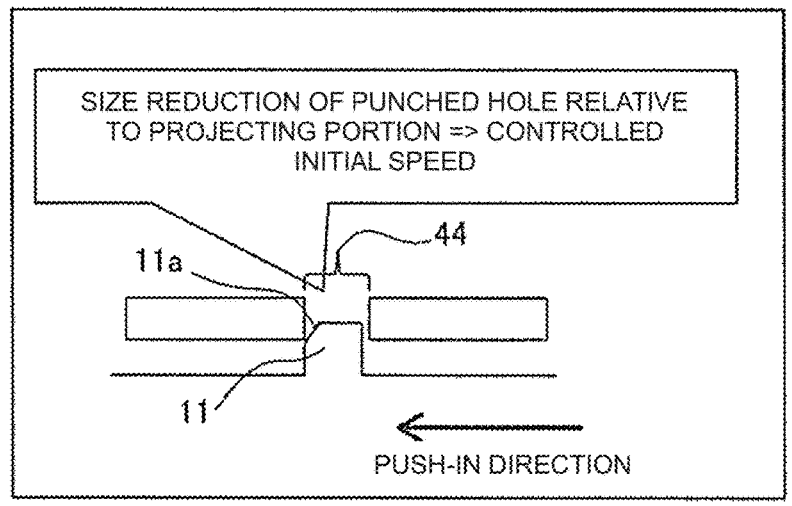
FIGS. 15(A) and 15(B) are conceptual drawings for explaining initial speed control and pushing speed control of the administration holder.
Figure 15B:
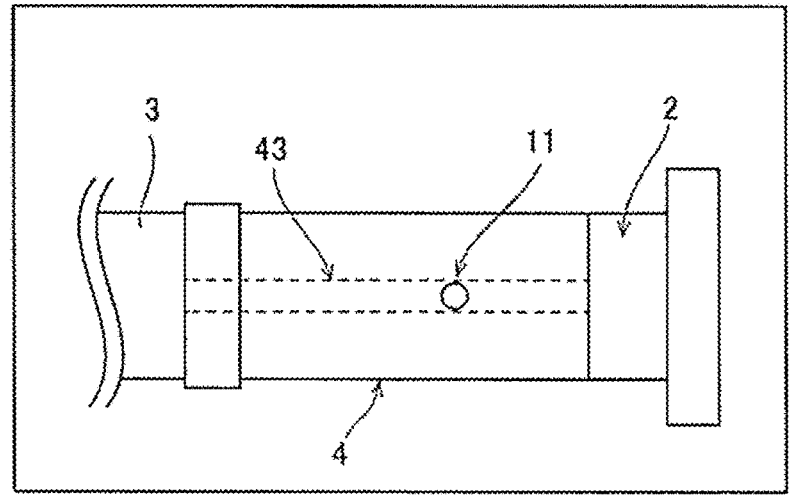

When the administration holder 2 is inserted from an initial position illustrated in FIG. 13(A) toward the coupling holder 3, the fitting state of the projecting portions 11 into the punched holes 44 of the administration holder 2 is released, and the projecting portions 11 move along guide slits 43 (see FIG. 15(B)), so that the administration holder 2 slides toward the coupling holder 3.

When the administration holder 2 slides from the initial position in FIG. 13(A) to a certain position, the rubber packing 70a comes into contact with the needle point 56, and the needle point 56 pricks the rubber packing 70a. When the administration holder 2 further slides, the rubber packing 70a pushes the needle point 56, and thus the double-ended needle assembly 5 starts to slide toward the second cartridge 102. Here, since a frictional force between the double-ended needle assembly 5 and the coupling holder 3 is set to be smaller than a frictional force between the needle point 56 and the rubber packing 70a, even when the administration holder 2 slides toward the cartridge 102, the double-ended needle assembly 5 is allowed to slide in a state in which the needle point 56 pricks the rubber packing 70a without penetrating therethrough.

Figure 13B:
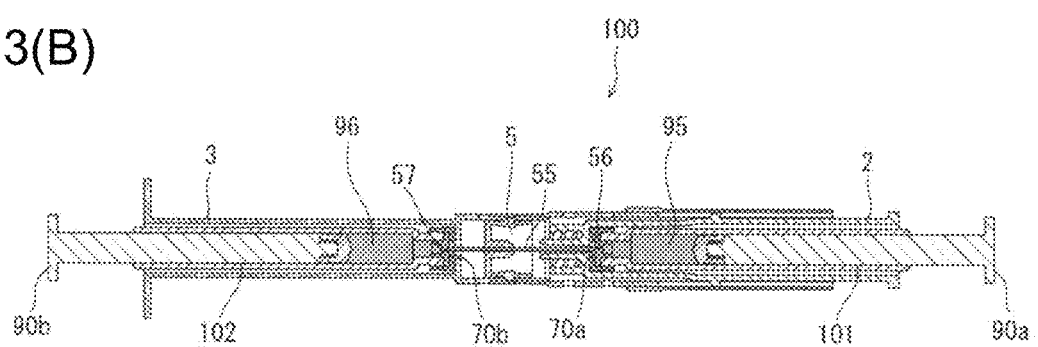

As illustrated in FIG. 13(B), when the double-ended needle assembly 5 further slides, the needle point 57 comes into contact with the rubber packing 70b of the second cartridge 102 and pricks the same in a state in which the needle point 56 pricks the rubber packing 70a without unsealing the same. In other words, since both of the needle points 56, 57 are in a state of pricking the rubber packings 70a, 70b respectively, openings at both ends of the double-ended needle 55 are closed.

Figure 13C:
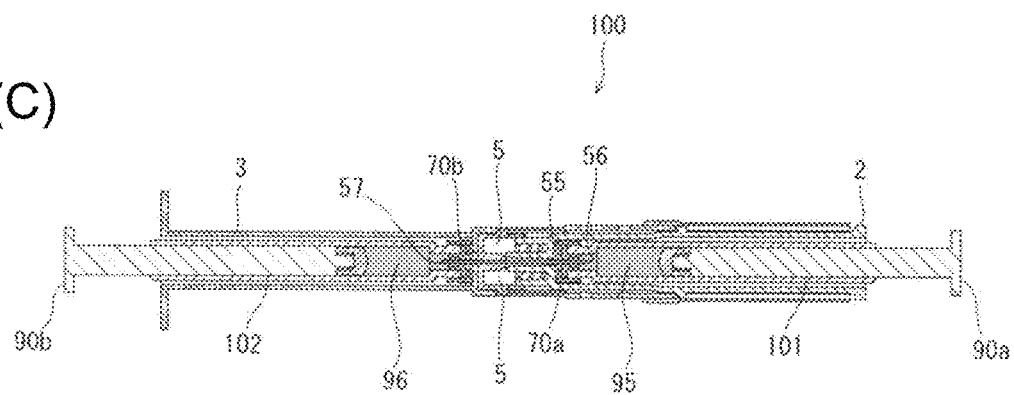

When the needle point 57 is in a state of pricking the rubber packing 70b of the second cartridge 102 as described above, a frictional force between the needle point 57 and the rubber packing 70b in addition to a frictional force between the double-ended needle assembly 5 and the coupling holder 3 is exerted against a force of sliding the administration holder 2. Therefore, as illustrated in FIG. 13(C), the needle point 56 unseals the rubber packing 70a and the needle point 57 unseals the rubber packing 70b before the double-ended needle assembly 5 further slides and reaches the closest position to the second cartridge 102 (a second position). Alternatively, the needle point 56 unseals the rubber packing 70a and the needle point 57 unseals the rubber packing 70b before the rubber packing 70a of the first cartridge 101 reaches a predetermined position (a position of the rubber packing 70a when the administration holder 2 is pushed to the maximum). In this manner, as illustrated in FIG. 13(C), the needle points 56, 57 of the double-ended needle 55 reaches the freeze-dry product 95 and the solvent 96 respectively, and the freeze-dry product 95 and the solvent 96 are allowed to communicate to each other through the needle through hole 58.

In the communicating state illustrated in FIG. 13(C), mixture of substances filled in the cartridges 101, 102 is achieved by pushing the plunger rod 90a, 90b attached respectively to the cartridges 101, 102 alternately. In a case of an example in which the cartridge 101 is filled with the freeze-dry product 95 and the cartridge 102 is filled with the solvent 96, the plunger rod 90b of the cartridge 102 on the solvent 96 side is pushed first to move the substantially entire solvent 96 to the cartridge 101 side through the double-ended needle 55 and causes the freeze-dry product 95 to be dissolved in the solvent 96, thereby forming a mixed solution. Subsequently, the plunger rod 90a is pushed to return the mixed solution on the cartridge 101 side back to the empty cartridge 102.

By repeatedly performing the above-described operation by a plurality of times, the solvent 96 and the freeze-dry product 95 may be sufficiently dissolved. Finally, after the entire mixed solution is returned back to the cartridge 101 side, the administration holder 2 is removed from the cylinder portion 6. By mounting a needle (not illustrated) on the needle insertion portion 12 of the administration holder 2 and pushing the plunger rod 90a, the mixed solution in the interior of the cartridge 101 may be administrated to a patient.

Irrespective of the position of the double-ended needle assembly 5 between the first position FIG. 13(A) and the second position (FIG. 13(C)), the needle point 56 is positioned closer to the cartridge 101 relative to the position of the rubber packing 70a in FIG. 13(C) (the predetermined position) when the administration holder 2 is pushed to the maximum. Accordingly, the needle point 56 pricks the rubber packing 70a in association with the movement from the position of the administration holder 2 in FIG. 13(A), the double-ended needle assembly 5 slides, and finally the rubber packing 70a is penetrated therethrough.

A prick process from FIG. 13(A) to 13(C) will be described with reference to further simplified FIGS. 14(A) to 14(C).

Figure 14A:
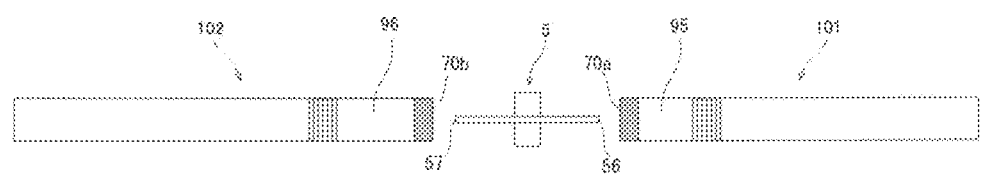
FIGS. 14(A), 14(B), and 14(C) are drawings schematically illustrating respective steps in FIGS. 13(A) to 13(C) until the double-ended needle of the double-ended needle assembly penetrates through the first cartridge and the second cartridge.

FIG. 14(A) illustrates a positional relationship among the cartridges 101, 102 and the double-ended needle assembly 5 before the prick operation. Before the prick operation, the needle points 56, 57 of the double-ended needle assembly 5 are not in a state of pricking the rubber packings 70a, 70b of the cartridges 101, 102.

Figure 14B:
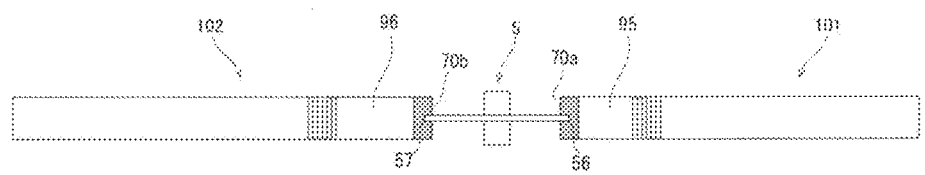

Subsequently, as illustrated in FIG. 14(B), the cartridge 101 moves toward the double-ended needle assembly 5 and the needle point 56 pricks the rubber packing 70a by a sliding movement of the administration holder 2 and, in this state, the cartridge 101 advances, and thus the double-ended needle assembly 5 also slides. As the double-ended needle assembly 5 advances toward the cartridge 102, the needle point 57 of the double-ended needle on the cartridge 102 side lightly pricks the rubber packing 70b of the cartridge 102. Accordingly, both of the needle points of the double-ended needle are in a closed state.

Figure 14C:
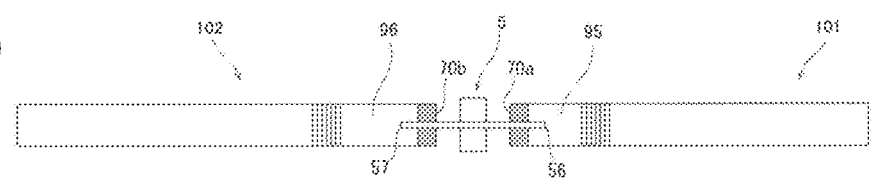

Finally, as illustrated in FIG. 14(C), the needle points of the double-ended needle penetrate through rubber packings of the cartridge 101 and the cartridge 102 by a further movement of the cartridge 101. The order of occurrence of penetration is not limited or may be the penetration may occur simultaneously. According to the embodiment of the invention of the present application, both of the needle points of the double-ended needle are brought into the closed state once as illustrated in FIG. 14(B), and then the double-ended needle unseals the cartridge 101 and the cartridge 102, and thus entry of air from needle points of the double-ended needle and leakage of the solvent may be prevented.

Figure 16:
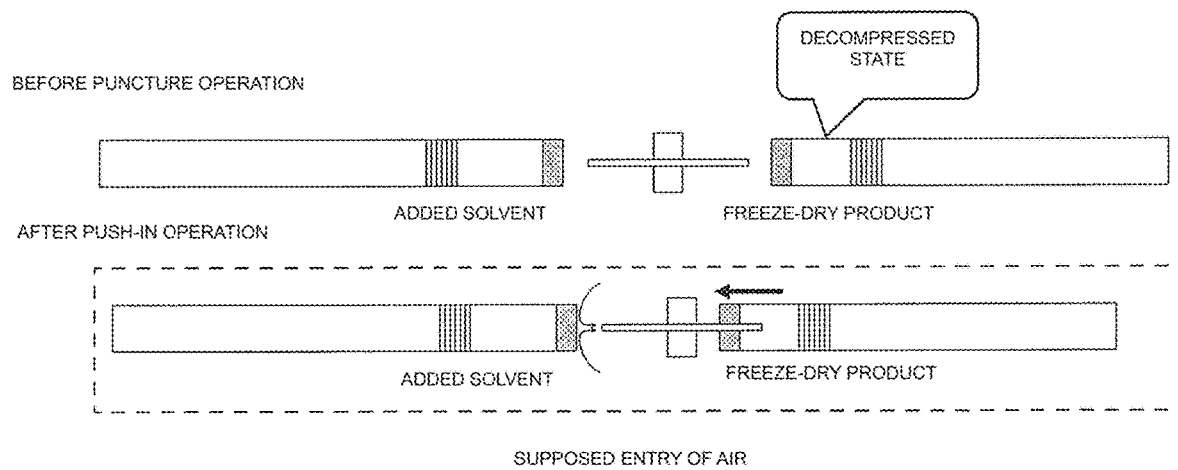
FIG. 16 is a drawing illustrating a problematic point which may occur when the double-ended needle assembly does not slide.

For example, with a syringe device of the related art configured in such a manner that when one of needle points of a double-ended needle assembly unseals the cartridge for a freeze-dry product first, other needle point does not reach a cartridge for a solvent as illustrated in FIG. 16, air enters the freeze-dry product in a decompressed state from the other needle point through a through hole of the needle, so that a remarkable increase in volume by entry of bubbles cannot be avoided when mixing the freeze-dry product and the solvent. In addition, when the syringe device is configured to unseal the solvent cartridge first as well, if the other needle point does not reach the cartridge for the freeze-dry product, liquid leakage from the other needle point may occur. In the invention of the present application, as the cartridge is unsealed after both of the needle points of the double-ended needle are brought into the closed state (FIG. 14(B)), the problem as illustrated in FIG. 16 may be prevented.

In addition, according to the embodiment of the present invention, the cartridge for the freeze-dry product and the solvent cartridge may be brought into communication with each other only with the double-ended needle by one operation, that is, by pushing the administration holder 2 in one direction, and thus improvement in terms of hygiene and operability is achieved. In addition, the cartridge for solvent and the cartridge for freeze-dry product in a state of being mounted in the holder in advance may be provided to the user (FIG. 13(A)). Therefore, a labor of the user for mounting the cartridge may be eliminated.

In addition, according to the embodiment, an initial speed when starting pushing the administration holder 2 may be controlled by selecting a diameter of the punched hole 44 in the slit holder 4 relative to a dimension of the projecting portions 11 of the administration holder 2 as needed. For example, as illustrated in FIG. 15(A), inclined portions 11a are provided at distal portions of the projecting portions 11 which engage the punched holes 44, the diameter of the punched holes 44 is set to be smaller than the dimension of the projecting portions 11 so as to achieve an engagement with the punched holes 44 via the inclined portions 11a. In this configuration, a resistance force generated when the administration holder 2 is pushed, and the inclined portions 11a are dislodged from the punched holes 44 to allow the administration holder 2 to start moving may be adjusted by selecting the diameter of the punched holes 44, so that the initial speed of the administration holder may be adjusted as needed.

In addition, as illustrated in FIG. 15(B), a width of the guide slits 43 relative to a width of the projecting portions 11 of the administration holder 2 may be selected as needed to control the speed of the administration holder 2 while being pushed. An adequate pushing speed is achieved by adjusting the width of the projecting portions 11 and the width of the guide slits 43 so as to come into tight contact with each other for making an adequate resistance force between the projecting portions 11 and the guide slits 43 adequate.

By the pushing speed control of the administration holder as described above, coring (a phenomenon in which rubber chips are scraped and mixed in a drug) at the time of prick of the needle point into the rubber packing may be prevented.

Although the embodiment of the present invention is described thus far, the present invention is not limited to examples described above, and may be changed optionally and desirably within the scope of the present invention.

For example, the cartridge 101 for the freeze-dry product is mounted in the administration holder 2 and the cartridge 102 for solvent is mounted in the coupling holder 3 in the example described above. However, a reverse arrangement is also applicable as a matter of course. In this case, in the procedure in FIG. 13(A), the plunger rod 90a on the solvent side is pushed first.

Although the cylinder portion 6 for allowing insertion of the administration holder 2 used here includes the coupling holder 3 and the slit holder 4 coupled to each other in the example described above, a configuration in which the coupling holder 3 and the slit holder 4 are integrally molded and a configuration in which the cylinder portion 6 is divided in a different manner as the division into the coupling holder and the slit holder may be applicable. The cylinder portion 6 as such may have any configuration as long as a cartridge containing one of substances to be mixed can be mounted, a segment which allows a sliding movement of the double-ended needle assembly 5 is provided, and the insertion of the administration holder 2 is allowed.

In addition, the first position and the second position described above of the double-ended needle assembly 5 do not have to be the rightmost position and the leftmost position of the double-ended needle assembly 5 in the double-ended needle sliding space 35, and may be positions shifted from the rightmost position and the leftmost position.

Communication between the first and second cartridges may be completed before the double-ended needle assembly 5 reaches the second position. Alternatively, communication between the first and second cartridge may be completed by further pushing the administration holder 2 after the double-ended needle assembly 5 has reached the second position.

In addition, although the first cartridge 101 is mounted in the first storage chamber 19 and the second cartridge 102 is mounted in the second storage chamber 33 in the example described thus far, a configuration in which substances to be mixed are stored directly in the first storage chamber 19 and the second storage chamber 33 respectively is also applicable.

REFERENCE SIGNS LIST 1, 100 syringe device
2 administration holder
3 coupling holder
4 slit holder
5 double-ended needle assembly
6 cylinder portion
10 body segment
12 needle insertion portion
17 opening
19 first storage chamber
20 first body segment
21 second body segment
22 third body segment
23 fourth body segment
27 air hole
30 guide groove
32 opening
33 second storage chamber
38 guide slit
40 main body segment
41 engaging body segment
43 guide slit
44 punched hole
50 double-ended needle supporting member
51 pair of projecting portions
55 double-ended needle
56, 57 needle point
58 needle through hole
60 cartridge container
70, 70a, 70b rubber packing
80 cap
85 piston
90, 90a, 90b plunger rod
95 freeze-dry product
96 solvent
101 first cartridge
102 second cartridge

The invention claimed is:

1. A syringe device comprising:
an administration holder including a first storage chamber including a first cartridge mounted therein, the first cartridge being configured to store a first substance and having a first sealing member formed at a front end portion thereof;
a double-ended needle assembly including a first needle point and a second needle point; and
a cylinder portion, which is hollow and includes:
a holder sliding portion configured to slidably retain the administration holder inserted at least partly from a first end of the cylinder portion;
a second storage chamber provided on a second end of the cylinder portion that is opposite to the first end, the second storage chamber including a second cartridge mounted therein, the second cartridge being configured to store a second substance and having a second sealing member formed at a front end portion thereof facing the front end portion of the first cartridge; and
a double-ended needle sliding portion formed between the holder sliding portion and the second storage chamber, the double-ended needle assembly being capable of sliding in the double-ended needle sliding portion from a first position to a second position while the first needle point faces the holder sliding portion and the second needle point faces the second storage chamber;

wherein, when the administration holder is pushed inward in the holder sliding portion toward the second storage chamber, the double-ended needle assembly is moved from the first position by a force generated by the first needle point being pushed by the first sealing member of the first cartridge while the first needle point is maintained in a first state in which the first needle point pricks the first sealing member without unsealing the first sealing member, wherein, by being continually moved, the double-ended needle assembly achieves a closed state in which the first needle point is maintained in the first state and the second needle point pricks the second sealing member of the second cartridge without unsealing the second sealing member, and wherein, after achieving the closed state, the double-ended needle assembly continues moving to the second position, and achieves a communicating state in which the first sealing member of the first cartridge is unsealed by the first needle point and the second sealing member of the second cartridge is unsealed by the second needle point.

2. The syringe device according to claim 1, wherein the first cartridge and the second cartridge communicate with each other via the double-ended needle assembly after the unsealing the first sealing member of the first cartridge by the first needle point and the second sealing member of the second cartridge by the second needle point.

3. The syringe device according to claim 1, wherein the administration holder includes a projecting portion on an outer peripheral portion, wherein the holder sliding portion includes a punched hole configured to receive the projecting portion and retain the administration holder at an initial position, and a slit extending in a longitudinal direction of the holder sliding portion and configured to guide the projecting portion when the administration holder is moved from the initial position.

4. The syringe device according to claim 3, wherein a diameter of the punched hole is smaller than a width of the projecting portion, the projecting portion includes an inclined portion at a distal portion thereof, and an initial speed of pushing the administration holder is controlled by the inclined portion engaging the punched hole.

5. The syringe device according to claim 3, wherein a width of the slit relative to the width of the projecting portion is set to control a speed of the administration holder being pushed.

6. The syringe device according to claim 1, wherein the double-ended needle sliding portion comprises:

a hollow body configured to define an internal space in which the double-ended needle assembly slides;

a wall formed at a boundary between the hollow body and the second storage chamber and including a hole which allows the second needle point to pass through; and a guide groove formed on an inner peripheral wall of the hollow body and extending in a longitudinal direction of the double-ended needle sliding portion, the guide groove being configured to guide a movement of a projecting portion formed on the double-ended needle assembly.

7. The syringe device according to claim 1, wherein the first substance is a solid state drug, the second substance is a solvent capable of dissolving the solid state drug, or the second substance is a solid state drug, and the first substance is a solvent capable of dissolving the solid state drug, or both of the first substance and the second substance are mixable liquid-state drugs.

8. The syringe device according to claim 1, wherein each of the first cartridge and the second cartridge comprises:

a cartridge container having a distal end opening, a bottom opening, and a hollow portion;

a rubber packing configured to seal the distal end opening of the cartridge container;

a cap configured to fix the rubber packing; and a piston configured to be slidably inserted from the bottom opening into the hollow portion, the piston allowing a substance to be stored between the rubber packing and the piston, wherein each of the first sealing member and the second sealing member comprises the rubber packing, respectively.

9. The syringe device according to claim 8, comprising a plunger rod configured to be mounted on the piston.

10. The syringe device according to claim 1, wherein the administration holder includes a needle insertion portion formed at a position adjacent to the first storage chamber.

11. A method of communicating a first substance and a second substance to each other using a syringe device, the syringe device including an administration holder including a first cartridge configured to store the first substance, a cylinder portion which is hollow, a double-ended needle assembly including a first needle point and a second needle point, and a second cartridge configured to store the second substance, the method comprising:

sliding the administration holder inserted into the cylinder portion along a longitudinal direction of the cylinder portion;

sliding the double-ended needle assembly by sliding the administration holder in a first state in which the first needle point pricks a first sealing member of the first cartridge without unsealing the first sealing member, wherein the double-ended needle assembly is moved by a force generated by the first needle point which is being pushed by the first sealing member of the first cartridge while the first needle point is maintained in the first state, while the first needle point is maintained in the first state, allowing the second needle point to prick a second sealing member of the second cartridge without unsealing the second sealing member before the first needle point unseals the first sealing member of the first cartridge, thereby forming a closed state of the double-ended needle assembly in which the first needle point is maintained in the first state and the second needle point pricks the second sealing member without unsealing the second sealing member; and after the closed state is formed, unsealing the first sealing member of the first cartridge and the second sealing member of the second cartridge, by the first needle point and the second needle point, respectively, by further sliding the administration holder, thereby allowing the first cartridge and the second cartridge to communicate with each other through the double-ended needle assembly.

12. The method according to claim 11, wherein the sliding the administration holder includes sliding the administration holder along the longitudinal direction of the cylinder portion in one-step continuous operation.

13. The method according to claim 11, wherein, after the allowing the first cartridge and the second cartridge to communicate with each other through the double-ended needle assembly, the method includes:
mixing the first substance and the second substance by pushing one substance, from among the first substance and the second substance, that is included in one cartridge of the first cartridge and the second cartridge outward into other cartridge of the first cartridge and the second cartridge through the double-ended needle assembly, and then pushing the first substance and the second substance mixed in the other cartridge into the one cartridge to mix the first substance and the second substance.

14. The method according to claim 13, wherein mixing the first substance and the second substance is repeatedly performed a plurality of times.

15. The method according to claim 13, wherein the substance in the one cartridge to be pushed out first is a liquid, and the substance in the other cartridge is a solid substance or a liquid.

16. The method according to claim 11, further comprising:
holding the administration holder at an initial position in the cylinder portion before sliding the administration holder, and
controlling an initial speed of the administration holder by adjusting a resistance force generated when starting the administration holder to slide from the initial position.

17. The method according to claim 11, wherein the sliding the administration holder further comprises:
adjusting a frictional force generated between the administration holder and the cylinder portion so as to control a sliding speed while pushing the administration holder.

18. The method according to claim 11, wherein, in the allowing the first cartridge and the second cartridge to communicate with each other through the double-ended needle assembly, one of the following operations is performed:
a first operation in which the first needle point unseals the first sealing member of the first cartridge and then the second needle point unseals the second sealing member of the second cartridge;
a second operation in which the second needle point unseals the second sealing member of the second cartridge and then the first needle point unseals the first sealing member of the first cartridge; or
a third operation in which the first needle point unseals the first sealing member of the first cartridge and simultaneously, the second needle point unseals the second sealing member of the second cartridge.

* * * * *